United States Patent [19]

Jones et al.

[11] Patent Number: 5,869,700
[45] Date of Patent: *Feb. 9, 1999

[54] METHOD FOR RECOVERING PHTHALIC ANHYDRIDE/MALEIC ANHYDRIDE MIXTURES BY DISTILLATION

[75] Inventors: Larry O. Jones, Baton Rouge, La.; James J. Baiel, Morris Plains, N.J.

[73] Assignee: Exxon Chemical Patents Inc., Houston, Tex.

[ * ] Notice: The term of this patent shall not extend beyond the expiration date of Pat. Nos. 5,718,808 and 5,508,443.

[21] Appl. No.: 803,681

[22] Filed: Feb. 21, 1997

[51] Int. Cl.$^6$ .................. C07D 307/89; C07D 307/60
[52] U.S. Cl. .................. 549/250; 549/258; 549/259; 203/60
[58] Field of Search .................. 549/250, 259; 203/60

[56] References Cited

U.S. PATENT DOCUMENTS

| | | | |
|---|---|---|---|
| 3,178,452 | 4/1965 | Smith et al. | 260/346.4 |
| 3,303,203 | 2/1967 | Melnstein | 260/346.7 |
| 3,380,896 | 4/1968 | Scheiber et al. | 203/77 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Gehrken et al. | 203/28 |
| 3,681,399 | 8/1972 | Barth | 260/346.7 |
| 3,725,211 | 4/1973 | Gehrken et al. | 203/74 |
| 4,285,870 | 8/1981 | Keunecke et al. | 260/346.7 |
| 4,285,871 | 8/1981 | Keunecke et al. | 260/346.7 |
| 4,568,427 | 2/1986 | Danz et al. | 203/42 |
| 5,214,157 | 5/1993 | Healy et al. | 549/250 |
| 5,508,443 | 4/1996 | Dengler et al. | 549/250 |
| 5,631,387 | 5/1997 | Brown et al. | 549/259 |
| 5,718,808 | 2/1998 | Baiel et al. | 549/250 |
| 5,730,844 | 3/1998 | Baiel et al. | 203/56 |
| 5,731,443 | 3/1998 | Dengler et al. | 549/248 |

FOREIGN PATENT DOCUMENTS

| 1121645 | 4/1956 | France | 14/1 |
|---|---|---|---|

*Primary Examiner*—Bernard Dentz
*Attorney, Agent, or Firm*—Andrew B. Griffis

[57] ABSTRACT

A process for recovering phthalic anhydride and maleic anhydride from a maleic anhydride-rich vapor phase oxidation product comprising the step of: contacting the vapor phase oxidation product with: (i) at least one by-product stream having a freezing point which is lower than the freezing point of pure phthalic anhydride; and/or (ii) a solvent having a boiling point in the range between about 150° to 350° C. and a freezing point of less than 40° C.; wherein a vapor-to-liquid weight ratio in the range between about 2 to 20 is exhibited within the contacting means, thereby forming a liquid phase phthalic anhydride product having a phthalic anhydride concentration in the range between about 50–100 wt. % and a first vapor stream.

13 Claims, 3 Drawing Sheets

METHOD FOR RECOVERING PHTHALIC ANHYDRIDE/MALEIC ANHYDRIDE MIXTURES BY DISTILLATION

The present invention generally relates to a method and system for continuously recovering mixtures of maleic anhydride and phthalic anhydride from a maleic anhydride-rich vapor phase oxidation product without the formation of a solid phase using distillation with or without added solvent.

BACKGROUND OF THE INVENTION

Phthalic anhydride (PAN) and maleic anhydride (MAN) are important commercial chemicals useful in the manufacture of plasticizers, polyesters, alkyd resins and dyes.

Maleic anhydride is typically produced by air oxidation of butane, butene or benzene (e.g., 2–5 mole percent in air) in the presence of a vanadium/phosphorus catalyst. Selectivities are typically 60–70 mole percent for conversions ranging from 80 to approximately 100%. This oxidation process produces organic by-products such as light acids (e.g., acetic acid and acrylic acid).

A phthalic anhydride and maleic anhydride mixture is typically produced by oxidation of n-pentane in the presence of a selective oxidation catalyst, e.g., a vanadium phosphate oxide catalyst (VPO) or a molybdenum oxide catalyst. Vanadium phosphate oxide catalysts can be obtained, for example, from precursors prepared by either of two methods: (1) immediate precipitation of a solution containing vanadia in isobutanol and $H_3PO_4$ and (2) facilitating, before precipitation, the conditions for the intercalation of the isobutanol in the $VOPO_4$ hydrated phase. Catalysts were obtained from the precursors by in situ treatment under reaction conditions for the selective oxidation of n-pentane. Control of the stage of formation of the precursor is crucial for obtaining a selective catalyst for formation of phthalic anhydride (PAN). The preparation of $VOHPO_4.\frac{1}{2}H_2O$ via a full development of the $VOPO_4.2H_2O$ phase, containing intercalated isobutanol, seems to favor the adequate structure of the precursor which promotes the formation of PAN. By careful control of the preparation of the VPO precursor, e.g., controlling the isobutanol/water ratio, the final catalyst can lead to the desired PAN/MAN ratio.

The resulting vapor phase oxidation product from the catalytic air oxidation of butane, butene or benzene typically comprises: a reaction gas composed of nitrogen, oxygen, water, carbon dioxide, carbon monoxide, acetic acid, acrylic acid, maleic anhydride, maleic acid, and partial oxidation products. While the vapor phase oxidation product from the catalytic air oxidation of pentane typically comprises: a reaction gas composed of nitrogen, oxygen, water, carbon dioxide, carbon monoxide, maleic anhydride, acetic acid, acrylic acid, phthalic anhydride, and other partial oxidation products.

The aforementioned vapor phase oxidation products are typically first cooled to generate steam and then delivered to expensive switch condensers, where they are cooled to permit the desublimation of a crude phthalic anhydride from the gas. Thereafter, the crude phthalic anhydride is sent to a finishing section in order to produce substantially pure phthalic anhydride; whereas the crude maleic anhydride is taken overhead from the switch condenser as a vapor and then recovery by solvent absorption.

The switch condensers operate alternatively on cooling and heating cycles in order to first collect either the maleic anhydride or, in the case of a PAN/MAN mixture, phthalic anhydride as a solid and then melt it for removal from the condensers. The use of switch condensers to separate crude phthalic anhydride from a vapor phase oxidation product is described in U.S. Pat. No. 5,214,157, which is incorporated herein by reference. Typically, the reactor vapor phase oxidation product is cooled close to the solidification point 131° C. (268° F.) of phthalic anhydride and any condensed liquid is separated out before the remaining vapor enters the switch condensers. The switch condensers desublime the vapor phase oxidation product using the cold condenser oil, and then melt off the solid phase crude phthalic anhydride product using a hot condenser oil heated with steam.

A substantial amount of impurities exit switch condensers as part of the vapor stream, whereas the crude maleic anhydride or phthalic anhydride/maleic anhydride product is plated out on the heat exchange tubes as a solid during the cooling step and exits the switch condensers at the bottom as a liquid during the melting step. The vapor gases from the switch condensers are sent to waste gas incinerators where the by-products are destroyed by oxidation to carbon dioxide and water.

Unfortunately, switch condensers contribute to a significant portion of the capital and operating costs of a phthalic anhydride plant. Also, switch condensers operate in a batch mode on 3–6 hour cycles to desublime solid phthalic anhydride on the heat exchange tubes. Another problem associated with switch condensers is that they necessitate frequent maintenance which requires that designated switch condensers be taken out of service on a periodic basis. Maintenance of switch condensers is costly due to the high labor requirement and condenser down time.

The present inventors have developed a unique process scheme which avoids the need to use expensive switch condensers to recover either maleic anhydride or phthalic anhydride/maleic anhydride mixture from vapor phase oxidation products. This unique process continuously condenses and recovers phthalic and maleic anhydride by rectification without the formation of an intermediate solid phase, wherein the maleic anhydride is taken overhead and recovered from the other overhead by-products by means of distillation. The rectification tower can be operated with or without the aid of a solvent which lowers the freezing point of the mixture contained therein so as to avoid freezing of the overhead products in the top of the rectification tower and/or condenser. A liquid phthalic anhydride recovery process using a rectification tower is disclosed in co-pending U.S. patent application, Ser. No. 08/431,647, (Dengler et al.), filed on May 2, 1995 now U.S. Pat. No. 5,731, 443, and which is incorporate herein by reference. The liquid phthalic anhydride recovery process disclosed in U.S. patent application, Ser. No. 08/431,647, (Dengler et al.) is based on concentrating the indigenous maleic anhydride (MAN) and benzoic acid (BA) co-products produced in the phthalic anhydride (PAN) reactor to form a minimum freezing MAN/BA/PAN mixture in the rectification tower condenser system. The present inventors have discovered that this condensing temperature is critical to the liquid phthalic anhydride recovery process and must: (1) be low enough to recover sufficient MAN to insure the liquid distillate will not freeze; and (2) be high enough to avoid free water from condensing thereby forming excessive amounts of acids in the distillate.

However, Dengler et al. does not pertain to the recovery of maleic overhead by means of distillation, rather it discloses a process for recovering maleic as a liquid from a vapor phase oxidation product which comprises mixing the vapor phase oxidation product with reaction by-products in a contacting means such that a substantial portion of the maleic anhydride contained within the vapor phase oxidation product transfers from the vapor phase to a liquid phase and the by-products contained in the reaction by-products which are more volatile than maleic anhydride transfer from the liquid phase to the vapor phase.

Dengler et al. also does not describe or suggest the use of a solvent to lower the freezing point of the mixture contained within the rectification tower. Therefore, the present invention provides a unique method for recovering large quantities of phthalic anhydride without the need for expensive switch condensers.

A similar conventional technique for recovery maleic anhydride is to scrub the reaction off-gas with a solvent to remove maleic anhydride before the off-gas is exhausted to an incinerator. The rich solvent stream is heated and vacuum stripped to release the maleic anhydride. Crude maleic anhydride is condensed and sent to purification. Stripped solvent is cooled and returned to the maleic anhydride absorber. A solvent slipstream is withdrawn for purification. Thereafter, the crude maleic anhydride is fractionated to remove light ends. The small quantity of by-product light ends is delivered to the incinerator for destruction and waste heat recovery. The maleic anhydride is further fractionated to separate any solvent and heavies which accompanied it in the stripper overhead. The bottoms stream is returned to the maleic anhydride stripper. A special step is included to remove any solvent degradation products from the slipstream, in order to prevent the build-up of impurities in the solvent recycle loop.

The process for absorption in an organic solvent as discussed immediately above is very expensive in terms of both hardware and consumable organic solvent. The maleic anhydride recovery using distillation with or without a solvent provides a significant advance in terms of cost and processing time verses the conventional solvent absorption process. The unique process according to the present invention uses distillation as a maleic anhydride recovery technique. The process according to the present invention recovers maleic anhydride from any gas stream resulting from any of the current oxidation processes, without the restrictions of the current technology.

The substantial technical differences between using absorption versus rectification for separating out maleic anhydride from a vapor phase oxidation gas product without the formation of an intermediate solid phase can be understood by comparing the vapor to liquid weight ratios (V/L) in the absorbent tower against the V/L for the rectification tower. For example, the V/L for the absorbent tower U.S. Pat. No. 4,285,871 (Keunecke '871), as calculated from the example provided therein is 0.3 to 0.7. The rectification tower of the present invention exhibits a V/L ratio of between 5 to 20, more preferably 8 to 15. That is, due to the substantial pumparound or recycling of the bottoms stream which is required in any absorbent case, its V/L ratio is only a fraction of that which occurs during rectification. The low V/L ratio in the absorbent case of Keunecke '871 clearly demonstrates that due to these high pumparound rates the absorbent tower is not providing any noticeable degree of separation of liquid maleic anhydride from a vapor phase maleic anhydride, such as that recited in the present invention.

Therefore, the advantages of the recovery processes of the present invention over the conventional solvent absorption processes discussed above are in simplification of process concept and elimination of adsorption and stripping steps required for the commercial solvent absorption process.

The present invention also provides a unique method for recovering maleic anhydride from a vapor phase oxidation product formed from the air oxidation of butane, butene and benzene by taking the maleic anhydride overhead as a vapor stream. This recovery process utilizes a uniquely tailored solvent which enlarges the window of operation for the condenser by reducing the freezing point of the condenser reflux, compared to the freezing point of maleic anhydride, and allows the condenser to operate at a lower temperature; thereby reducing the amount of maleic anhydride in the vapor stream exiting the condenser.

The solvent, taken overhead and condensed with the maleic anhydride in the condenser, forms a condensate which provides the liquid reflux to the rectification tower. In the rectification tower, the liquid reflux stream is stripped of the maleic anhydride by the hot vapor phase oxidation product and the residual solvent in the liquid phase is removed as a bottoms stream from the tower. The vapor phase maleic anhydride, recovered as liquid in the condensate, is then distilled from a portion of this liquid phase and the residual solvent from this distilled portion of the condensate stream is returned to the rectification tower. The liquid condensate from the condenser also contains low boiling, compared to maleic anhydride, by-products from the oxidation reaction such as acetic acid and acrylic acid.

Further, the use of a tailored solvent-enhanced recovery process is beneficial when maleic anhydride and phthalic anhydride are co-produced as a vapor phase oxidation product. The present inventors have discovered that the addition of a small amount of a selected solvent to a MAN/PAN mixture substantially reduces the freezing point of the total mixture. More importantly, the present inventors have discovered that the addition of a solvent to concentrations of 5 to 10 mole percent to the MAN/PAN mixtures obtained as the liquid reflux to the rectification tower is sufficient to reduce the freezing point of the MAN/PAN mixtures and allows recovery of both MAN and PAN by means of simple distillation.

The present inventors have developed a modification to the liquid phthalic anhydride recovery process disclosed in co-pending U.S. patent application, Ser. No. 08/431,647, (Dengler et al.). The present invention provides for the addition of a solvent to the rectification tower reflux system to lower the freezing point of the PAN/MAN mixture. In addition, the solvent according to the present invention will increase the low temperature operating region and broaden the potential application of the maleic anhydride or phthalic anhydride/maleic anhydride recovery process In summary, using a specifically tailored solvent in the maleic anhydride or PAN/MAN mixture recovery process: (1) allows for the choosing of a tailored component with properties better than maleic anhydride (MAN) reflux to reduce the freezing point of the maleic anhydride/phthalic anhydride mixture; (2) provides a low freezing point operating region sufficiently large for good commercial plant operation and control; and (3) frees the liquid recovery process of the present invention from depending on the maleic anhydride and other reaction by-products to lower the freezing point of the liquid condensate, the rectification tower reflux, sufficiently to recover either maleic anhydride (MAN only) or maleic anhydride and phthalic anhydride with high efficiency by simple distillation means.

SUMMARY OF THE INVENTION

A process for recovering phthalic anhydride and maleic anhydride from a maleic anhydride-rich vapor phase oxidation product of $C_5$ to $C_8$ hydrocarbons having a temperature at its dew point temperature or greater; the process comprises the step of: delivering the vapor phase oxidation product to a contacting means which is capable of causing the vapor phase oxidation product to come into contact with: (i) at least one by-product stream having a freezing point which is lower than the freezing point of pure phthalic anhydride; and/or (ii) a solvent having a boiling point in the range between about 150° to 350° C. and a freezing point of less than 40° C.; such that a substantial portion of the phthalic anhydride contained within the vapor phase oxidation product transfers from the vapor phase to a liquid phase and a substantial portion of the solvent and/or by-product stream is more volatile than phthalic anhydride and is transferred from the liquid phase to the vapor phase and wherein a vapor-to-liquid weight ratio in the range between about 2 to 20 is exhibited within the contacting means, thereby forming a liquid phase phthalic anhydride product having a phthalic anhydride concentration in the range between about 50–100 wt. % and a first vapor stream.

The process may further comprise the steps of: (a) removing the liquid phase phthalic anhydride product from the contacting means as bottoms; (b) removing the vapor phase maleic anhydride product from the contacting means as overhead; (c) cooling the vapor phase maleic anhydride product to a temperature in the range between about 25° C. to 80° C., thereby forming a first liquid stream comprising the solvent, a first by-product stream comprising a crude maleic anhydride product and light-ends by-products, and a first vapor stream; (d) separating the first liquid stream from the first vapor stream; (e) separating the solvent and crude maleic anhydride product from the light-ends by-products; (f) separating the solvent and the crude maleic anhydride product into a solvent-enriched stream and a substantially pure maleic anhydride product; and (g) recycling at least a portion of the solvent-enriched stream to the upper section of the contacting means.

A substantial portion of the phthalic anhydride contained within the vapor phase oxidation product transfers from the vapor phase to a liquid phase and a substantial portion of the by-product stream is more volatile than phthalic anhydride.

The process further comprises the steps of separating the liquid phase phthalic anhydride product into a crude phthalic anhydride stream and a second vapor phase which comprises the solvent; and condensing the second vapor phase and blending it with the first by-product stream and the solvent from step (d).

Typically, between about 0 to 50 wt. % of the liquid phase phthalic anhydride product of step (a) is recycled to the contacting means, whereby the liquid phase phthalic anhydride product is only used for temperature and composition control.

The solvent is preferably at least one solvent selected from the group consisting of: adipates, maleates, phthalates, carbonates, benzoates, ketones, aromatics, anhydrides, halogenated hydrocarbons, halogenated oxy hydrocarbons, ether acetates, naphthalenes, ethers, and esters. More specifically, the solvent is at least one solvent selected from the group consisting of: dimethyl adipate, diethyl adipate, dipropyl adipate, dibutyl adipate, dihexyl adipate, diheptyl adipate, dioctyl adipate, dinonyl adipate, dimethyl maleates, diethyl maleates, propylene carbonate, propyl benzoate, isobutyl benzoate, isophorone, e-caprolactone, isobutyl heptyl ketone, di-normal amyl ketone, di-isoamyl ketone, hexyl benzene, mixed aromatics, n-valeric anhydride, $C_9$ alkyl acetate ester, $C_{10}$ alky acetate ester, 1,4-butanediol diacetate, malonic acid-dipropyl ester, dimethyl phthalates, and esters of $C_5$ to $C_{10}$ neo acids and mono-polyhydric alcohols.

The solvent may also be formed in situ by the addition of an alcohol to the contacting means, wherein the alcohol reacts with the maleic anhydride and/or the phthalic anhydride to form the desired solvent.

The $C_5$ to $C_8$ hydrocarbons are preferably selected from the group consisting of: pentanes, pentenes, hexanes, hexenes, heptanes, heptenes, octenes and octanes.

Moreover, the vapor phase oxidation product is typically formed by oxidation of n-pentane. The oxidation of the n-pentane occurs in the presence of a vanadium phosphate oxide catalyst or any other phthalic anhydride/maleic anhydride selective oxidation catalyst, thereby forming a vapor phase oxidation product comprising maleic anhydride and phthalic anhydride.

Finally, the above process further comprises the step of adding additional solvent to the solvent-enriched stream in order to make-up for solvent losses.

The process according to another embodiment of the present invention may be used in recovering maleic anhydride from a vapor phase oxidation product of butanes, butenes and benzenes having a temperature at its dew point temperature or greater; the process comprises the step of: delivering the vapor phase oxidation product to a contacting means which is capable of causing the vapor phase oxidation product to come into contact with: (i) at least one byproduct stream having a freezing point which is lower than the freezing point of pure maleic anhydride; and/or (ii) a solvent having a boiling point in the range between about 150° to 350° C. and a freezing point of less than 40° C.; such that a substantial portion of the maleic anhydride contained within the vapor phase oxidation product transfers from the vapor phase to a liquid phase to the vapor phase and wherein a vapor-to-liquid weight ratio in the range between about 2 to 20 is exhibited within the contacting means, thereby forming a liquid phase maleic anhydride product having a maleic anhydride concentration in the range between about 50–100 wt. % and a solvent-rich vapor phase stream.

The above used in recovering maleic anhydride from a vapor phase oxidation product of butanes, butenes and benzenes may also comprise the below steps: (a) removing the liquid phase maleic anhydride product from the contacting means as bottoms; (b) removing the solvent-rich vapor phase stream from the contacting means as overhead; (c) cooling the solvent-rich vapor phase stream to a temperature in the range between about 25° C. to 80° C., thereby formiing a liquid solvent-enriched stream comprising solvent, a crude maleic anhydride product, heavy by-products and light-ends by-products, and a first vapor stream; (d) separating the liquid solvent-enriched stream from the first vapor stream; (e) separating the crude maleic anhydride product and the solvent from the light-ends by-products; (f) separating the solvent and the crude maleic anhydride product into a first by-product stream and a substantially pure maleic anhydride product; and (g) recycling at least a portion of the first by-products stream to the upper section of the contacting means.

The solvents used when only maleic anhydride is recovered from a vapor phase oxidation product may be similar to those set forth above; provided that the solvent is chosen such that it has the following properties: (1) inert or only slightly reactive; (2) a boiling point greater than 150° C., but preferably a higher boiling point than maleic anhydride and low enough to be vaporized by hot oil or high pressure steam (for the PAN/MAN recovery discussed above, the solvent should exhibit an atmospheric boiling point up to 350° C., but preferably less than PAN); (3) a lower melting or freezing point than maleic anhydride; and (4) soluble with maleic anhydride or mixtures of maleic anhydride, PAN or other oxidation by-products.

DESCRIPTION OF THE PREFERRED EMBODIMENTS

Figure 1:
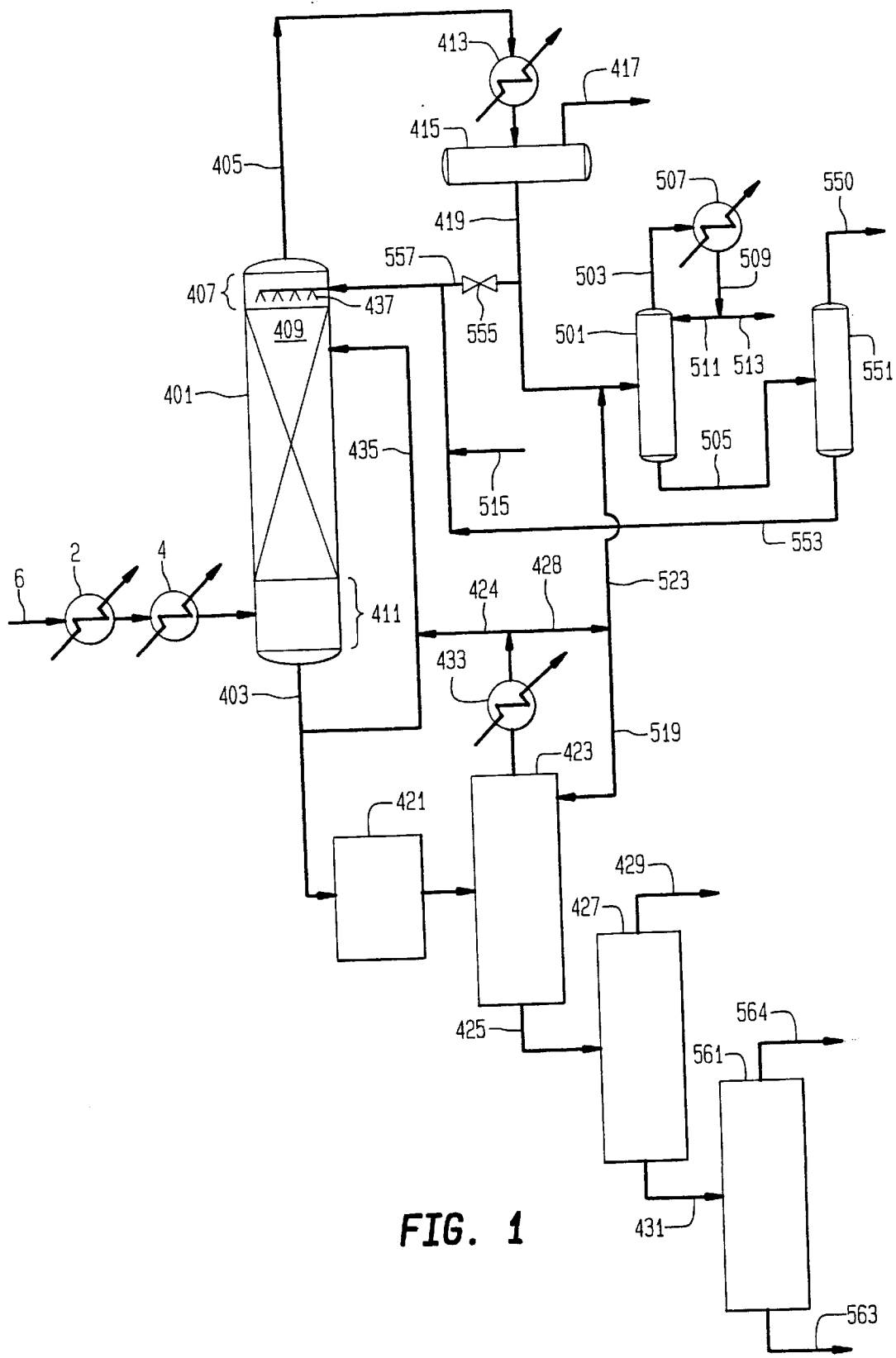
FIG. 1 is a schematic diagram of the phthalic anhydride/maleic anhydride recovery process in accordance with the preferred embodiment of the present invention wherein a low pressure gas/liquid contactor rectification tower is used in conjunction with external cooling and separating devices for recycling a low freezing point solvent back to the rectification tower, and wherein a pair of serially connected maleic anhydride recovery distillation towers are used to treat rectification tower overhead.

A continuous process for recovering phthalic anhydride (PAN) and maleic anhydride (MAN) from a vapor phase oxidation product of n-pentane or the like.

According to the present invention, the formation of crude liquid phthalic anhydride product without the presence of an intermediate solid phase phthalic anhydride is accomplished by contacting the vapor phase oxidation product with a solvent having a boiling point in the range between about 150° to 350° C. and a freezing point of less than 40° C., whereby the operating temperatures are always above the freezing point of the liquid phase. It is preferable that the contacting occur in a rectification tower so that a vapor-to-liquid weight ratio within the contacting tower is maintained in the range between about 2 to 20, more preferably 3 to 15.

Thus, it is a primary objective of the present invention to add a specifically tailored solvent to the liquid phthalic anhydride process described below which is capable of lowering the freezing point of the phthalic anhydride/maleic anhydride mixture. In addition, the present inventors have discovered that the uniquely tailored solvent will increase the low temperature operating region and broaden the potential application of the liquid phthalic anhydride process. The present inventors have also discovered that maleic anhydride which is taken overhead from the rectification tower can be readily separated from the solvent by means of distillation without the need for the absorption, stripping and fractionation steps disclosed in the conventional maleic recovery processes.

A preferred solvent candidate must exhibit the following properties: (1) have good solvency for the mixture so as to achieve maximum freezing point depression at low solvent concentrations; (2) have a volatility lower than maleic anhydride so as to minimize the solvent lost to the incinerator gas, but higher than phthalic anhydride to enable recovery and recycle of any solvent that breaks through the liquid phthalic anhydride tower as bottoms; (3) have a low pure component freezing point; and (4) be chemically inert.

The most desirable solvents for the liquid phthalic anhydride recovery process are those with an aromatic ring and/or oxygen in the structure. These types of solvent structures promote solubility of the phthalic anhydride, maleic anhydride, and other by-products in the solvent. The most preferred solvents are those which have a boiling point in the range between about 150° to 350° C., preferably 200 to 284° C., and most preferably 213° to 270° C., and a freezing point of less than 40° C. The best solvent family groups are adipates, carbonates, benzoates, ketones, aromatics, anhydrides, halogenated hydrocarbons, halogenated oxy hydrocarbons, ether acetates, naphthalenes, ethers and esters.

Set forth below are the more volatile solvents in each of the above-identified solvent families along with their boiling and melting points:

| Solvent | Boiling Point (°C.) | Melting Point (°C.) |
|---|---|---|
| ADIPATES | | |
| dimethyl adipate | 235 | 0 |
| diethyl adipate | 240 | −21 |
| CARBONATES | | |
| propylene carbonate | 242 | −49 |
| BENZOATES | | |
| propyl benzoate | 229 | −52 |
| isobutyl benzoate | 242 | |
| KETONES | | |
| isophorone | 215 | −8 |
| e-caprolactone | 235 | −2 |
| isobutyl heptyl ketone | 213–224 | −10 |
| di-normal amyl ketone | 228 | 14 |
| di-isoamyl ketone | 226 | 15 |
| AROMATICS | | |
| hexyl benzene | 226 | −61 |
| narrow cut mixed aromatics solvent | (Aromatic 200 range) | −26 |
| ANHYDRIDES | | |
| n-valeric anhydride | 227 | −49 |
| ESTERS | | |
| $C_9$ alkylacetate ester | 205–234 | −60 |
| $C_{10}$ alkylacetate ester | 220–250 | −60 |
| 1,4-butanediol diacetate | 229 | 12 |
| malonic acid-dipropyl ester | 229 | −70 |
| malonic acid-dibutyl ester | 251 | −83 |
| phthalic acid-dimethyl ester | 282 | 2 |
| maleic acid-dimethyl ester | 205 | −19 |
| maleic acid-diethyl ester | 225 | −88 |
| $C_5$–$C_{10}$ neo acid-polyol ester | | |

The preferred less volatile solvents are the higher boiling homologues of the above families, such as dipropyl adipate, dibutyl adipate, dihexyl adipate, dioctyl adipate, and dinonyl adipate.

The preferred embodiment according to the present invention involves the configuration depicted in FIG. 1. This figure pertains to the use of a contacting or packed tower having either an external cooling/condensing system.

However, the cooling/condensing system can also be internal to the tower.

FIG. 1 describes a process for recovering maleic anhydride and liquid phthalic anhydride from a vapor phase oxidation product. The vapor phase oxidation product of n-pentane or any other material capable of being catalytically converted to a mixture of phthalic anhydride and maleic anhydride is passed via conduit 6 through heat exchangers 2 and 4 wherein the vapor phase oxidation product is cooled to its dew point temperature or greater. The cooled vapor phase oxidation product is delivered from conduit 6 to rectifier or contacting means 401 which is capable of causing the vapor phase oxidation product to come into contact with a solvent having a boiling point in the range between about 150° to 350° C. and a freezing point of less than 40° C. so that a vapor-to-liquid weight ratio in the range between about 2 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a vapor phase maleic anhydride product stream. Rectification tower 401 separates the liquid phase phthalic anhydride product from the vapor phase maleic anhydride product stream by means of multiple equilibrium stages, i.e., packing or trays, (not shown) disposed therein. Rectifier tower 401 is typically a low pressure drop countercurrent gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 401 due to the choice of operating conditions.

The liquid phase phthalic anhydride product is removed from rectifier tower 401 as bottoms via conduit 403, while the vapor phase maleic anhydride product stream is removed from rectifier tower 401 as overhead via conduit 405. Rectifier tower 401 has an upper section 407, an intermediate section 409 and a lower section 411.

The vapor phase maleic anhydride product stream taken overhead via conduit 405 is passed through a heat exchanger or low pressure drop gas cooler 413 where it is cooled to a temperature in the range between about 25° C. to 80° C. (77°–176° F.), thereby forming a first by-product comprising a crude maleic anhydride product, acetic acid, acrylic acid and other heavy oxidation by-products and solvent stream, and a first vapor stream. This mixed phase stream is then delivered to a vapor/liquid disengaging drum 415 wherein the first by-product stream and solvent stream are separated from the first vapor stream. The first vapor stream is then taken out overhead via conduit 417 for disposal via incineration. The first by-product and solvent stream are taken out as bottoms from drum 415 via conduit 419 and delivered to a fractionation or distillation tower 501, wherein the acetic acid and acrylic acid are taken overhead via conduit 503 and the crude maleic anhydride product, other heavy oxidation by-products and solvent are taken as bottoms via conduit 505.

The overhead stream taken from fractionation tower 501 via conduit 503 is preferably cooled via heat exchanger 507 and recycled to the top of tower 501 via conduits 509 and 511 and purged from the system via conduits 509 and 513. The bottoms from fractionation tower 501 are preferably sent to fractionation tower 551 wherein substantially pure maleic anhydride is taken overhead via conduit 550 and wherein solvent and the heavy oxidation by-products are recycled via conduit 553 to top portion 407 of rectification tower 401 in order to maintain the proper vapor to liquid ratio therein such that the freezing point of the PAN/MAN mixture is lowered, thereby avoiding freezing and providing a larger operating range in rectification tower 401. If necessary, make-up solvent can be added to rectification tower 401 via conduits 515 and 553.

Alternatively, liquid condensate from drum 415 can be diverted via valve 555 and conduit 557 directly to rectification tower 401 if additional maleic anhydride is needed to maintain the proper vapor to liquid ratio in tower 401 and also to prevent freezing of the mixture contained therein.

The liquid phase phthalic anhydride product which is removed from rectification tower 401 as bottoms preferably has a concentration of between about 50–100 wt. %, more preferably between about 90–100 wt. %, and most preferably between about 95–99.8 wt. %, phthalic anhydride.

The liquid phase phthalic anhydride product passes via conduit 403, optionally, into at least one decomposer 421 which operates under a slight vacuum (about 700 mm Hg absolute) and high temperatures (e.g., 260° C. (500° F.)) to convert the small amount of phthalic acid that is present to phthalic anhydride. Thereafter, the liquid phase phthalic anhydride product is pumped from decomposer 421 to a light-ends column or fractionation column 423 wherein a second by-product and solvent stream comprising low-boiling by-products, e.g., maleic anhydride, along with some solvent are removed at the top of fractionation column 423, cooled via heat exchanger 433, and at least a part of this stream is optionally returned to rectifier tower 401 as a second by-product and solvent stream via conduits 424 and 435 with the remainder of the stream being recycled to the top of fractionation column 423 via conduits 428 and 519, and blended with the first by-products and solvent stream being sent to fractionation tower 501 by means of conduits 523 and 419.

Crude phthalic anhydride is taken as bottoms from fractionation column 423 and is optionally fed via conduit 425 to fractionation column 427 wherein substantially pure phthalic anhydride is removed from the top of fractionation column 427 via conduit 429, while heavy products are removed from the bottom via conduit 431. If a heavy solvent is used, then it is separated from the heavy products via fractionation tower 561, wherein heavies are taken out the bottom via conduit 563 and heavy solvent is removed overhead via conduit 564 and returned to tower 401.

Optionally, a small portion (i.e., 0–10%) of the liquid phase phthalic anhydride product removed as bottoms from rectifier tower 401 via conduit 403 is recycled via conduit 435 to rectifier tower 401 for temperature and concentration control in the tower.

Overall recovery of the phthalic anhydride from the reactor effluent gas (i.e., vapor phase oxidation product) is approximately 99.7% for process described in FIG. 1.

The vapor phase oxidation product fed into the system via conduit 6 is preferably formed by oxidation of n-pentane in the presence of a PAN/MAN selective oxidation catalyst, preferably a vanadium phosphate oxide catalyst, thereby forming a vapor phase oxidation product comprising maleic anhydride and phthalic anhydride. The following is an example preparation procedure of a vanadium oxide phosphate catalyst which is preferably obtained from precursors prepared by either: (i) by immediate precipitation of a solution containing vanadia in isobutanol and $H_3PO_4$; or (ii) by facilitating, before precipitation, the conditions for the intercalation of the isobutanol in the $VOPO_4$ hydrated phase, as described in Sobalik et al., Influence of the Precursor Formation Stage in the Preparation of VPO Catalysts for Selective Oxidation of n-Pentane, *Study of Surfactant Science Catalysts*, Elsevier Science B.V., 1995, pp. 727–736, which is incorporated herein by reference.

Figure 2:
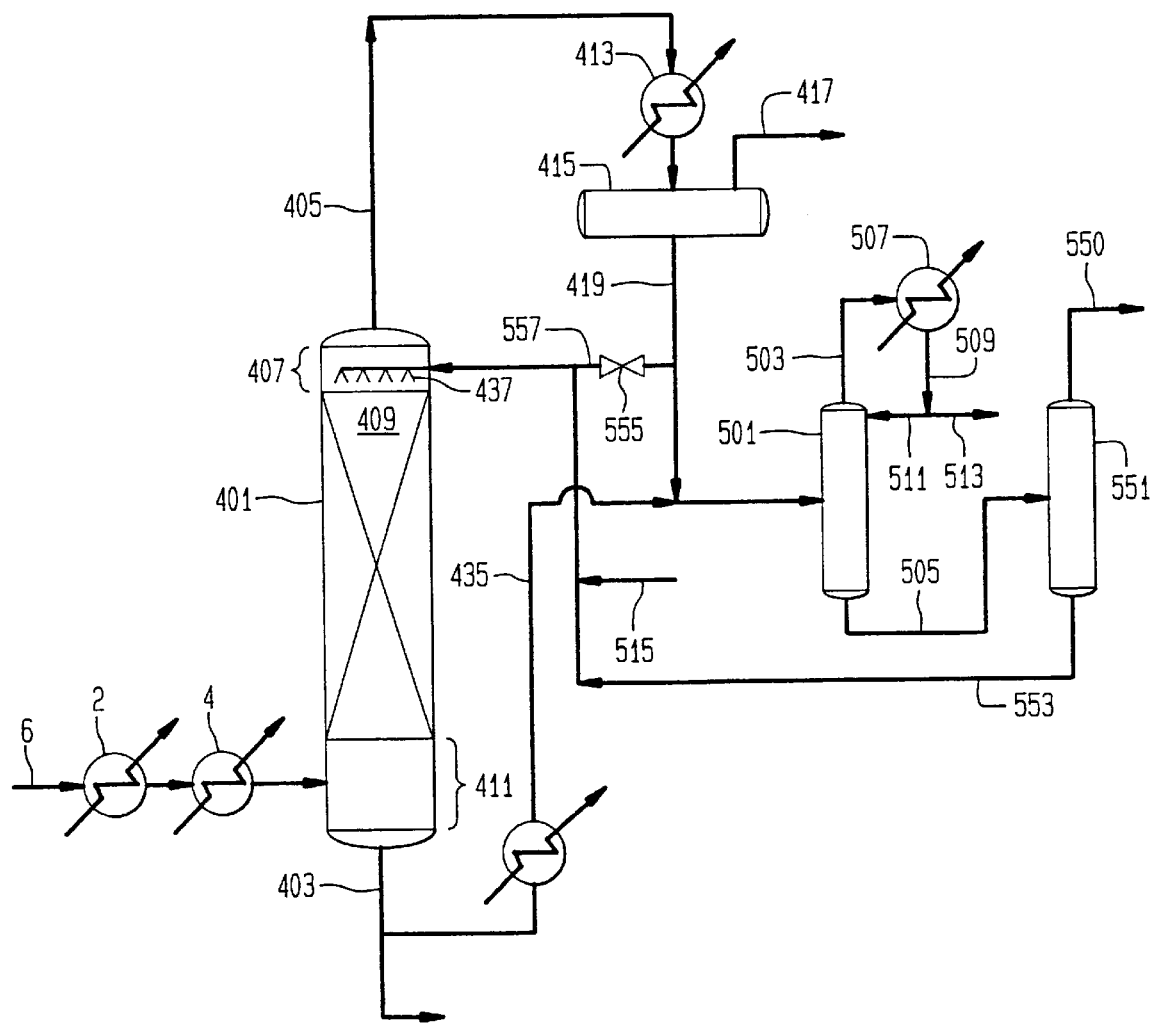
FIG. 2 is schematic diagram of the maleic anhydride recovery process in accordance with another embodiment of the present invention wherein a low pressure gas/liquid contactor rectification tower is used in conjunction with external cooling and separating devices for recycling a low freezing point solvent back to the rectification tower, and wherein a pair of serially connected maleic anhydride recovery distillation towers are used to treat rectification tower overhead.

FIG. 2 depicts a maleic anhydride recovery process according to the present invention. The vapor phase oxidation product of butane, butene or benzene or any other material capable of being catalytically converted to maleic anhydride is passed via conduit 6 through heat exchangers 2 and 4 wherein the vapor phase oxidation product is cooled to its dew point temperature or greater. The cooled vapor phase oxidation product is delivered from conduit 6 to rectifier or contacting means 401 which is capable of causing the vapor phase oxidation product to come into contact with a solvent having a boiling point in the range between about 150° to 350° C. and a freezing point of less than 40° C. so that a vapor-to-liquid weight ratio in the range between about 2 to 20 is maintained, thereby forming a solvent-rich vapor phase and a liquid phase maleic anhydride product stream. Rectification tower 401 separates the solvent-rich vapor phase from the liquid phase maleic anhydride product stream by means of multiple equilibrium stages, i.e., packing or trays, (not shown) disposed therein. Rectifier tower 401 is typically a low pressure drop counter-current gas/liquid contactor having at least 2 low pressure drop equilibrium stages, preferably 3 to 10.

It should be kept in mind that despite operating below the freezing point of maleic anhydride there is no formation of a solid phase anywhere within rectifier tower 401 due to the choice of operating conditions.

The liquid phase maleic anhydride is removed from rectifier tower 401 as bottoms via conduit 403, while the solvent-rich vapor phase stream is removed from rectifier tower 401 as overhead via conduit 405. Rectifier tower 401 has an upper section 407, an intermediate section 409 and a lower section 411.

The solvent-rich vapor phase stream taken overhead via conduit 405 is passed through a heat exchanger or low pressure drop gas cooler 413 where it is cooled to a temperature in the range between about 25° C. to 80° C., thereby forming a liquid solvent-enriched stream comprising solvent, a crude maleic anhydride product, heavy by-products and light-ends by-products and a first vapor stream. This mixed phase stream is then delivered to a vapor/liquid disengaging drum 415 wherein the liquid solvent-enriched stream is separated from the first vapor stream. The first vapor stream is then taken out overhead via conduit 417 for disposal via incineration. The liquid solvent-enriched stream is taken out as bottoms from drum 415 via conduit 419 and delivered to a fractionation or distillation tower 501, wherein the light-ends by-products (i.e., acetic acid and acrylic acid) are taken overhead via conduit 503 and the solvent, the crude maleic anhydride product and heavy by-products are taken as bottoms via conduit 505.

The overhead stream taken from fractionation tower 501 via conduit 503 is preferably cooled via heat exchanger 507 and recycled to the top of tower 501 via conduits 509 and 511 and purged from the system via conduits 509 and 513. The bottoms from fractionation tower 501 are preferable sent to fractionation tower 551 wherein substantially pure maleic anhydride is taken overhead via conduit 550 and wherein solvent and the heavy oxidation by-products are recycled via conduit 553 to top portion 407 of rectification tower 401 in order to maintain the proper vapor to liquid ratio therein such that the freezing point of the contents of tower 401 is lower than pure maleic anhydride, thereby avoiding freezing and providing a larger operating range in rectification tower 401. If necessary, makeup solvent can be added to rectification tower 401 via conduits 515 and 553.

Alternatively, liquid condensate from drum 415 can be diverted via valve 555 and conduit 557 directly to rectification tower 401 if additional maleic anhydride is needed to maintain the proper vapor to liquid ratio in tower 401 and also to prevent freezing of the contents of tower 401.

The vapor phase oxidation product used in the embodiment of FIG. 2 is formed by oxidation of either butane, butene or benzene in the presence of an oxidation catalyst, selective for maleic anhydride, such as a vanadium phosphorus oxide catalyst, thereby forming a vapor phase oxidation product comprising maleic anhydride at 60–100% conversion of the feed.

It is also possible that solvent can be formed in situ within rectification tower 401 by the addition of an appropriate alcohol via conduit 515 (e.g., methanol, ethanol, propyl, butyl, hexyl, heptyl and octyl alcohol) which reacts with the anhydrides contained therein to form an ester, primarily esters of maleic anhydride, which meets the criteria for solvents set forth above.

Figure 3:
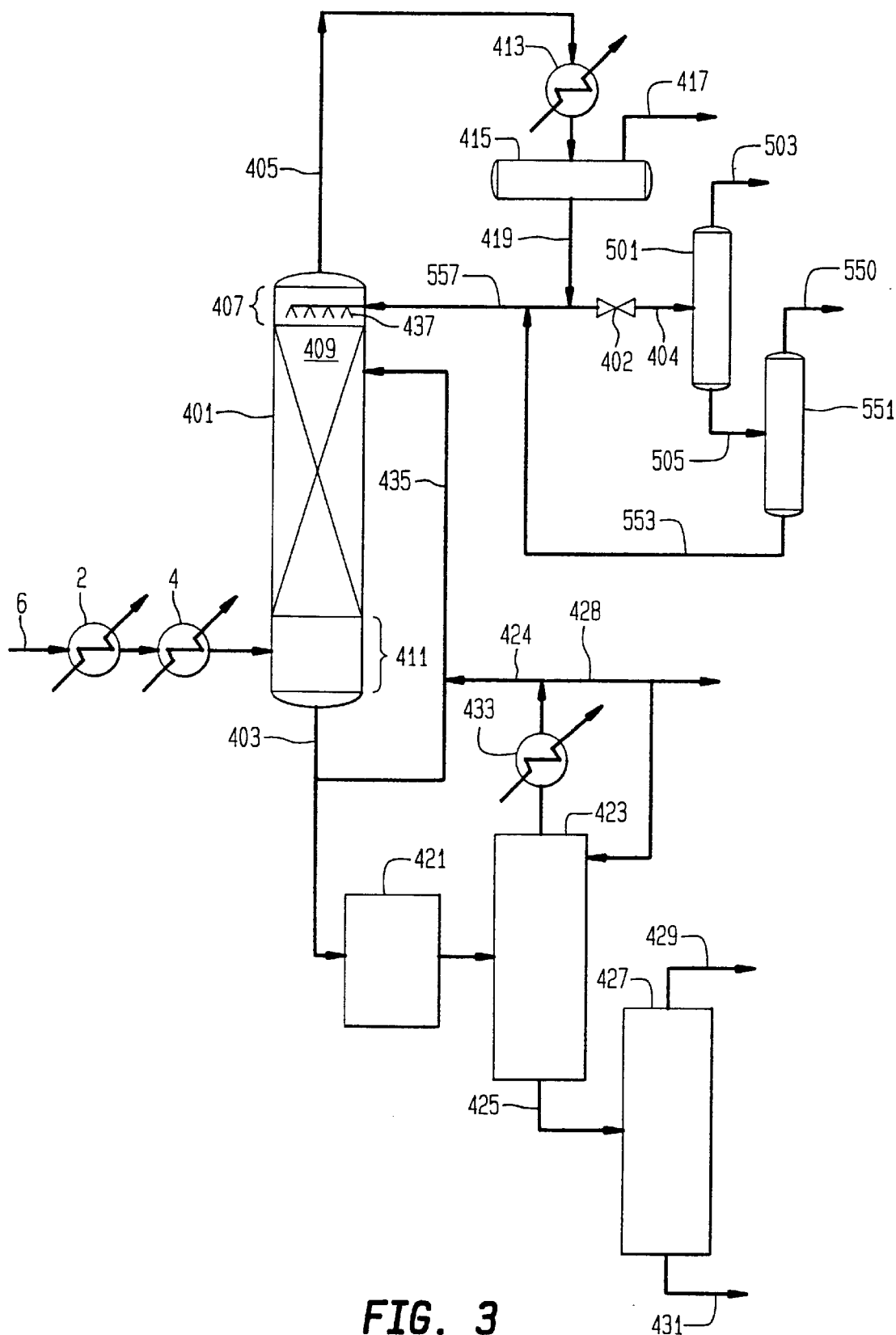
FIG. 3 is a schematic diagram of a phthalic anhydride/maleic recovery process in accordance with another embodiment of the present invention wherein a low pressure gas/liquid contactor rectification tower is used in conjunction with external cooling and separating devices for recycling a by-products stream back to the rectification tower, and wherein a pair of serially connected maleic anhydride recovery distillation towers are used to treat rectification tower overhead.

FIG. 3 describes a process for recovering phthalic anhydride as a liquid from a vapor phase oxidation product. The vapor phase oxidation product of n-pentane or any other material capable of being catalytically converted to a mixture of phthalic anhydride and maleic anhydride is passed via conduit 6 through heat exchangers 2 and 4 wherein the vapor phase oxidation product is cooled to its dew point temperature or greater. The cooled vapor phase oxidation product is delivered from conduit 6, following cooling to a temperature no lower than its dew point, to rectifier or contacting means 401 which is capable of causing the vapor phase oxidation product to come into contact with first by-products stream (i.e., maleic anhydride, phthalic anhydride and other reaction by-products) a vapor-to-liquid weight ratio in the range between about 2 to 20 is maintained, thereby forming a liquid phase phthalic anhydride product having a phthalic anhydride concentration of between about 50–100 wt. %, preferably between about 85–100 wt. %, more preferably about 90–100 wt. %, and most preferably between about 95–99.8 wt. %, and a vapor phase maleic anhydride product stream. Rectification tower 401 separates the liquid phase phthalic anhydride product from the vapor phase maleic anhydride product stream by means of multiple equilibrium stages, i.e., packing or trays, (not shown) disposed therein. Rectifier tower 401 is typically a low pressure drop counter-current gas/liquid contactor having at least 2 low pressure drop equilibrium stages, preferably 3 to 10.

It should be kept in mind that despite operating below the freezing point of phthalic anhydride there is no formation of a solid phase anywhere within rectifier tower 401 due to the choice of operating conditions.

The liquid phase phthalic anhydride product is removed from rectifier tower 401 as bottoms via conduit 403, while the vapor phase maleic anhydride product stream is removed from rectifier tower 401 as overhead via conduit 405. Rectifier tower 401 has an upper section 407, an intermediate section 409 and a lower section 411.

The vapor phase maleic anhydride product stream taken overhead via conduit 405 is passed through a heat exchanger or low pressure drop gas cooler 413 where it is cooled to a temperature in the range between about 25° C. to 80° C., thereby forming a first by-product comprising a crude maleic anhydride product, acetic acid, acrylic acid and other heavy oxidation by-products, and a first vapor stream. This mixed phase stream is then delivered to a vapor/liquid disengaging drum 415 wherein the first by-product stream is separated from the first vapor stream. The first vapor stream is then taken out overhead via conduit 417 for either further maleic recovery or disposal via incineration. The first by-products stream is taken out as bottoms from drum 415 via conduit 419 and delivered to upper portion 407 of tower 401 or diverted by means of valve 402 and conduit 404 to fractionation or distillation tower 501, wherein the acetic acid and acrylic acid are taken overhead via conduit 503 and the crude maleic anhydride product and other heavy oxidation by-products are taken as bottoms via conduit 505.

The bottoms from fractionation tower 501 are preferable sent to fractionation tower 551 wherein substantially pure maleic anhydride is taken overhead via conduit 550 and wherein the heavy oxidation by-products are recycled via conduits 553 and 419 to top portion 407 of rectification tower 401 in order to maintain the proper vapor to liquid ratio therein such that the freezing point of the PAN/MAN mixture is lowered, thereby avoiding freezing and providing a larger operating range in rectification tower 401. Optionally, bottoms from fractionation tower 501 may be taken to a holding tank for treatment to reduce the color thereof prior to distillation in fractionation tower 551.

The liquid phase phthalic anhydride product which is removed from rectification tower 401 as bottoms preferably has a concentration of between about 50–100 wt. %, more preferably between about 90–100 wt. %, and most preferably between about 95–99.8 wt. %, phthalic anhydride.

The liquid phase phthalic anhydride product passes via conduit 403, optionally, into at least one decomposer 421 which operates under a slight vacuum (about 700 mm Hg absolute) and high temperatures (e.g., 260° C. (500° F.)) to convert the small amount of phthalic acid that is present to phthalic anhydride and to reduce color bodies. Thereafter, the liquid phase phthalic anhydride product is pumped from decomposer 421 to a light-ends column or fractionation column 423 wherein a second by-products stream comprising low-boiling by-products are removed at the top of fractionation column 423, cooled via heat exchanger 433, and at least a part of this stream is optionally returned to rectifier tower 401 as a second by-products stream via conduits 424 and 435 with the remainder of the stream being sent to incineration or other disposal via conduit 428 and returned to column 423.

Crude phthalic anhydride is taken as bottoms from fractionation column 423 and is optionally fed via conduit 425 to fractionation column 427 wherein substantially pure phthalic anhydride is removed from the top of fractionation column 427 via conduit 429, while heavy products are removed from the bottom via conduit 431.

Optionally, a portion (i.e., 0–50%) of the liquid phase phthalic anhydride product removed as bottoms from rectifier tower 401 via conduit 403 is recycled via conduit 435 to rectifier tower 401 for temperature and concentration control in the tower.

Overall recovery of the phthalic anhydride from the reactor effluent gas (i.e., vapor phase oxidation product) is approximately 99.7% for process described in FIG. 3.

The vapor phase oxidation product fed into the system via conduit 6 preferably formed by oxidation of n-pentane in the presence of a VPO catalyst, thereby forming a vapor phase oxidation product comprising maleic anhydride and phthalic anhydride, as discussed above in FIG. 1.

What is claimed is:

1. A process for recovering phthalic anhydride and maleic anhydride from a maleic anhydride-rich vapor phase oxidation product of $C_5$ to $C_8$ hydrocarbons having a temperature at its dew point temperature or greater; said process comprises the step of:

delivering said vapor phase oxidation product to a contacting means which is capable of causing said vapor phase oxidation product to come into contact with:
    (i) at least one by-product stream having a freezing point which is lower than the freezing point of pure phthalic anhydride; and/or
    (ii) a solvent having a boiling point in the range between about 150° to 350° C. and a freezing point of less than 40° C.;

such that a substantial portion of the phthalic anhydride contained within said vapor phase oxidation product transfers from the vapor phase to a liquid phase and a substantial portion of said solvent and/or by-product stream is more volatile than phthalic anhydride and is transferred from the liquid phase to the vapor phase and wherein a vapor-to-liquid weight ratio in the range between about 2 to 20 is exhibited within said contacting means, thereby forming a liquid phase phthalic anhydride product having a phthalic anhydride concentration in the range between about 50–100 wt. % and a first vapor stream.

2. The process according to claim 1 wherein said solvent is at least one solvent selected from the group consisting of: adipates, maleates, phthalates, carbonates, benzoates, ketones, aromatics, anhydrides, halogenated hydrocarbons, halogenated oxy hydrocarbons, ether acetates, naphthalenes, ethers, and esters.

3. The process according to claim 2 wherein said solvent is at least one solvent selected from the group consisting of: dimethyl adipate, diethyl adipate, dipropyl adipate, dibutyl adipate, dihexyl adipate, diheptyl adipate, dioctyl adipate, dinonyl adipate, dimethyl maleates, diethyl maleates, propylene carbonate, propyl benzoate, isobutyl benzoate, isophorone, e-caprolactone, isobutyl heptyl ketone, di-normal amyl ketone, di-isoamyl ketone, hexyl benzene, mixed aromatics, n-valeric anhydride, $C_9$ alkyl acetate ester, $C_{10}$ alky acetate ester, 1,4-butanediol diacetate, malonic acid-dipropyl ester, dimethyl phthalates, and esters of $C_5$ to $C_{10}$ neo acids and mono-polyhydric alcohols.

4. The process according to claim 1 further comprising the steps of:

(a) removing said liquid phase phthalic anhydride product from said contacting means as bottoms;
    (b) removing said vapor phase maleic anhydride product from said contacting means as overhead;
    (c) cooling said vapor phase maleic anhydride product to a temperature in the range between about 25° C. to 80° C., thereby forming a first liquid stream comprising said solvent, a first by-product stream comprising a crude maleic anhydride product and light-ends by-products, and a first vapor stream;
    (d) separating said first liquid stream from said first vapor stream;
    (e) separating said solvent and crude maleic anhydride product from said light-ends by-products;
    (f) separating said solvent and said crude maleic anhydride product into a solvent-enriched stream and a substantially pure maleic anhydride product; and
    (g) recycling at least a portion of said solvent-enriched stream to the upper section of said contacting means.

5. The process according to claim 1 wherein a substantial portion of the phthalic anhydride contained within said vapor phase oxidation product transfers from the vapor phase to a liquid phase and a substantial portion of said by-product stream is more volatile than phthalic anhydride.

6. The process according to claim 4 further comprising the step of:

separating said liquid phase phthalic anhydride product into a crude phthalic anhydride stream and a second vapor phase which comprises said solvent; and condensing said second vapor phase and blending it with said first by-product stream and said solvent from step (d).

7. The process according to claim 4 further comprising the step of recycling between about 0 to 50 wt. % of said liquid phase phthalic anhydride product of step (a) to said contacting means, whereby said liquid phase phthalic anhydride product is only used for temperature and composition control.

8. The process according to claim 1 wherein said $C_5$ to $C_8$ hydrocarbons are selected from the group consisting of: pentanes, pentenes, hexanes, hexenes, heptanes, heptenes, octenes and octanes.

9. The process according to claim 8 wherein vapor phase oxidation product is formed by oxidation of n-pentane.

10. The process according to claim 9 wherein the oxidation of said n-pentane occurs in the presence of a vanadium phosphate oxide catalyst or any other phthalic anhydride/maleic anhydride selective oxidation catalyst, thereby forming a vapor phase oxidation product comprising maleic anhydride and phthalic anhydride.

11. The process according to claim 10 wherein said vanadium phosphate oxide catalyst is obtained from precursors prepared by either: (i) by immediate precipitation of a solution containing vanadia in isobutanol and $H_3PO_4$; or (ii) by facilitating, before precipitation, the conditions for the intercalation of the isobutanol in the $VOPO_4$ hydrated phase.

12. The process according to claim 9 wherein the oxidation of said n-pentane occurs in the presence of a molybdenum oxide catalyst, thereby forming a vapor phase oxidation product comprising maleic anhydride and phthalic anhydride.

13. The process according to claim 4 further comprising the step of adding additional solvent to said solvent-enriched stream in order to make-up for solvent losses.

* * * * *